US010450554B2

(12) United States Patent
Van Der Laan et al.

(10) Patent No.: US 10,450,554 B2
(45) Date of Patent: Oct. 22, 2019

(54) PROLINE SPECIFIC ENDOPROTEASE

(71) Applicant: DSM IP ASSETS B.V., Heerlen (NL)

(72) Inventors: Jan Metske Van Der Laan, Echt (NL); Peter Jozef Ida Van De Vondervoort, Echt (NL); Chantal Christis, Echt (NL); Martine Spaans, Echt (NL); Angela De Bruine-Paulus, Echt (NL); Johanna Henrica Gerdina Maria Mutsaers, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 204 days.

(21) Appl. No.: 15/312,171

(22) PCT Filed: May 19, 2015

(86) PCT No.: PCT/EP2015/061026
§ 371 (c)(1),
(2) Date: Nov. 17, 2016

(87) PCT Pub. No.: WO2015/177171
PCT Pub. Date: Nov. 26, 2015

(65) Prior Publication Data
US 2017/0081651 A1    Mar. 23, 2017

(30) Foreign Application Priority Data

May 19, 2014   (EP) ..................... 14168866

(51) Int. Cl.
| | | |
|---|---|---|
| *A61K 38/48* | (2006.01) | |
| *C12N 1/20* | (2006.01) | |
| *C12N 9/62* | (2006.01) | |
| *A23L 2/84* | (2006.01) | |
| *A23J 3/34* | (2006.01) | |
| *C12N 9/50* | (2006.01) | |
| *A23L 2/66* | (2006.01) | |
| *A23L 7/10* | (2016.01) | |
| *A23L 33/18* | (2016.01) | |
| *A23L 33/195* | (2016.01) | |

(52) U.S. Cl.
CPC ................ *C12N 9/62* (2013.01); *A23J 3/347* (2013.01); *A23L 2/66* (2013.01); *A23L 2/84* (2013.01); *A23L 7/101* (2016.08); *A23L 33/18* (2016.08); *A23L 33/195* (2016.08); *C12N 9/50* (2013.01); *C12Y 304/21026* (2013.01)

(58) Field of Classification Search
CPC ................ C12Y 304/21026; A61K 38/486
See application file for complete search history.

(56) References Cited

U.S. PATENT DOCUMENTS

| | | | |
|---|---|---|---|
| 7,309,595 B2 | 12/2007 | Dekker et al. | |
| 7,608,697 B2 | 10/2009 | Edens et al. | |
| 8,119,171 B2* | 2/2012 | Lopez ...................... | A23J 3/16 |
| | | | 424/94.63 |
| 2010/0112635 A1 | 5/2010 | Edens et al. | |

FOREIGN PATENT DOCUMENTS

| | | |
|---|---|---|
| CN | 1484497 A | 3/2004 |
| WO | 03/104382 A1 | 12/2003 |
| WO | 2012/174127 A1 | 12/2012 |
| WO | 2013/135732 A1 | 9/2013 |
| WO | 2014/202622 A2 | 12/2014 |

OTHER PUBLICATIONS

Lopez et al. U.S. Pat. No. 8,119,171 sequence alignments with SEQ ID No. 1 and 2. 2018.*
International Search Report and Written Opinion of International Application No. PCT/EP2015/061026 dated Jul. 23, 2015.

* cited by examiner

*Primary Examiner* — Karen Cochrane Carlson
(74) *Attorney, Agent, or Firm* — McBee Moore Woodward & Vanik IP, LLC (57) ABSTRACT

The present invention relates to a polypeptide having proline-specific endoprotease activity, selected from the group consisting of
  i. a polypeptide comprising a mature polypeptide sequence of SEQ ID NO: 2;
  ii. a polypeptide that has least 70%, 75%, 80%, 85%, 86%, 87%, 88%, 89%, 90%, 91%, 92%, 93%, 94%, 95%, 96%, 97%, 98% or 99% identity to the mature polypeptide sequence of SEQ ID NO: 2;
  iii. a polypeptide encoded by a nucleic acid that hybridizes under medium stringency, preferably under high stringency conditions to the complementary strand of the mature polypeptide coding sequence of SEQ ID NO:1;
  iv. a polypeptide encoded by a nucleic acid that has at least 70%, 75% 80%, 85%, 90%, 91%, 92%, 93%, 94%, 95%, 96%, 97%, 98%, 99% or 100% identity to the mature polypeptide coding sequence of SEQ ID NO: 1.

The invention further relates to a method of producing the polypeptide and a process for the preparation of a food or feed product wherein the polypeptide is used.

21 Claims, 1 Drawing Sheet
Specification includes a Sequence Listing.

SEQUENCE LISTING

```
<160> NUMBER OF SEQ ID NOS: 6

<210> SEQ ID NO 1
<211> LENGTH: 1580
<212> TYPE: DNA
<213> ORGANISM: Artificial Sequence
<220> FEATURE:
<223> OTHER INFORMATION: Codon optimized nucleic acid encoding proline-
      specific endoprotease from Rasamsonia emersonii BC2G079 for
      expression in A. niger

<400> SEQUENCE: 1
atgccctccc tctcctccct cgttgccttg actgcttctc ttgtctctct ggctgctgcc      60
gctgctcctc gtctccctct tcctcctcgc cctcccttgc ctcccgtga ccccttgcac     120 ggacctacca acgcctccgc cactttccag cagctcatcg accacaacca ccccgagctt     180
ggcaccttct cccagcgcta ctggtggaat gatgagttct ggaagggtcc cggctctccc     240
gttgtccttt tcaccccgg tgaagaagat gccagcggtt acgtgggcta cctgaagaac     300
accaccatca ccggtctgat cgctcagacc atcggtggtg ccgtcatcgt cctcgaacac     360
cgctactggg gccagtcctc cccctacgac tctctgacca ccaagaacct gcagtacctg     420
accctcaagc agtccattgc cgacctcacc tacttcgcca agaccgtcaa gctccccttc     480
gaccgcaacg gcagctccaa cgccgacaag gctccctggg ttctcagcgg tggaagctac     540
tctggtgctc tctccgcctg gactgccagc acctccccg gtactttctg ggcctaccac     600
gccagctctg ctcctgttga ggccatctac gattactggc agtacttcgc tcccgtgcag     660
gatggattgc ctgccaactg ctcgaaggac ctctcccgtg tcgtcgacta catcgactcc     720
gttctccagt ccggcaacgc cactgccaag caacagctca ggaccttttt cggtctgggt     780
gctctggagc acgacgatga cttcgcctcc gctcttgaga acgcccttg gctctggcag     840 tcgaactcgt tctacgaccc ctaccctcct gtctacgagt ctgcgacta cgttgagaac     900 gcctacgcca gccctcccgt tgctgctggt cccgatggtg ttggtctgga aaggctctg     960 tctggctacg ccacctggtg gaacaaggtc ttcttccccg gctactgcgc tacctacggc    1020
tactggtcct ccaacgactc cattgcctgc ttcgacacct caaccagtc gtcgcccatg    1080 ttcaccgacc tttccgtctc caacactatc aaccgccagt ggaactggtt cctctgcaac    1140
gagcccttct tctactggca ggatggtgct cccaagaacg tccccagcat tgtctctcgt    1200
ctggtcactg ctgagtactg gcagcgccag tgccccttgt tcttccctga agaggatggc    1260
tacacctacg gaagcgccaa gggcaagact gctgccgatg tcaacgcctg gaccaagggc    1320
```

```
tggttcttga ctaacaccac ccgtctgatc tggaccaacg gcgagcttga cccctggcgc    1380
tctgctggtg tcagcagcaa gttccgtccc ggtggtcccc tccagtccac tccccaggct    1440
cctctgcagc tcattcccga gggtgtccac tgctacgatc tgatcctcaa gaacgccgag    1500
gccaacgccg tgtgcagcg tgttgtcacc aacgaggttg ctcagatcaa ggcctgggtg    1560
aacgaatact accgtaagta                                                1580

<210> SEQ ID NO 2
<211> LENGTH: 526
<212> TYPE: PRT
<213> ORGANISM: Artificial Sequence
<220> FEATURE:
<223> OTHER INFORMATION: Rasamsonia emersonii

<400> SEQUENCE: 2

Met Pro Ser Leu Ser Ser Leu Val Ala Leu Thr Ala Ser Leu Val Ser
 1               5                  10                  15

Leu Ala Ala Ala Ala Pro Arg Leu Pro Leu Pro Pro Arg Pro Pro
            20                  25                  30

Leu Pro Pro Arg Asp Pro Leu His Gly Pro Thr Asn Ala Ser Ala Thr
 35                  40                  45

Phe Gln Gln Leu Ile Asp His Asn His Pro Glu Leu Gly Thr Phe Ser
 50                  55                  60

Gln Arg Tyr Trp Trp Asn Asp Glu Phe Trp Lys Gly Pro Gly Ser Pro
65                  70                  75                  80

Val Val Leu Phe Thr Pro Gly Glu Glu Asp Ala Ser Gly Tyr Val Gly
                85                  90                  95

Tyr Leu Lys Asn Thr Thr Ile Thr Gly Leu Ile Ala Gln Thr Ile Gly
            100                 105                 110

Gly Ala Val Ile Val Leu Glu His Arg Tyr Trp Gly Gln Ser Ser Pro
        115                 120                 125

Tyr Asp Ser Leu Thr Thr Lys Asn Leu Gln Tyr Leu Thr Leu Lys Gln
    130                 135                 140

Ser Ile Ala Asp Leu Thr Tyr Phe Ala Lys Thr Val Lys Leu Pro Phe
145                 150                 155                 160

Asp Arg Asn Gly Ser Ser Asn Ala Asp Lys Ala Pro Trp Val Leu Ser
                165                 170                 175

Gly Gly Ser Tyr Ser Gly Ala Leu Ser Ala Trp Thr Ala Ser Thr Ser
            180                 185                 190

Pro Gly Thr Phe Trp Ala Tyr His Ala Ser Ala Pro Val Glu Ala
        195                 200                 205

Ile Tyr Asp Tyr Trp Gln Tyr Phe Ala Pro Val Gln Asp Gly Leu Pro
    210                 215                 220

Ala Asn Cys Ser Lys Asp Leu Ser Arg Val Val Asp Tyr Ile Asp Ser
225                 230                 235                 240

Val Leu Gln Ser Gly Asn Ala Thr Ala Lys Gln Gln Leu Lys Asp Leu
                245                 250                 255

Phe Gly Leu Gly Ala Leu Glu His Asp Asp Phe Ala Ser Ala Leu
            260                 265                 270

Glu Asn Gly Pro Trp Leu Trp Gln Ser Asn Ser Phe Tyr Asp Pro Tyr
        275                 280                 285

Pro Pro Val Tyr Glu Phe Cys Asp Tyr Val Glu Asn Ala Tyr Ala Ser
    290                 295                 300

Pro Pro Val Ala Ala Gly Pro Asp Gly Val Gly Leu Glu Lys Ala Leu
```

```
                305                 310                 315                 320
Ser Gly Tyr Ala Thr Trp Trp Asn Lys Val Phe Phe Pro Gly Tyr Cys
                325                 330                 335

Ala Thr Tyr Gly Tyr Trp Ser Ser Asn Asp Ser Ile Ala Cys Phe Asp
                340                 345                 350

Thr Tyr Asn Gln Ser Ser Pro Met Phe Thr Asp Leu Ser Val Ser Asn
                355                 360                 365

Thr Ile Asn Arg Gln Trp Asn Trp Phe Leu Cys Asn Glu Pro Phe Phe
            370                 375                 380

Tyr Trp Gln Asp Gly Ala Pro Lys Asn Val Pro Ser Ile Val Ser Arg
385                 390                 395                 400

Leu Val Thr Ala Glu Tyr Trp Gln Arg Gln Cys Pro Leu Phe Phe Pro
                405                 410                 415

Glu Glu Asp Gly Tyr Thr Tyr Gly Ser Ala Lys Gly Lys Thr Ala Ala
                420                 425                 430

Asp Val Asn Ala Trp Thr Lys Gly Trp Phe Leu Thr Asn Thr Thr Arg
            435                 440                 445

Leu Ile Trp Thr Asn Gly Glu Leu Asp Pro Trp Arg Ser Ala Gly Val
450                 455                 460

Ser Ser Lys Phe Arg Pro Gly Gly Pro Leu Gln Ser Thr Pro Gln Ala
465                 470                 475                 480

Pro Leu Gln Leu Ile Pro Glu Gly Val His Cys Tyr Asp Leu Ile Leu
                485                 490                 495

Lys Asn Ala Glu Ala Asn Ala Gly Val Gln Arg Val Val Thr Asn Glu
                500                 505                 510

Val Ala Gln Ile Lys Ala Trp Val Asn Glu Tyr Tyr Arg Lys
            515                 520                 525

<210> SEQ ID NO 3
<211> LENGTH: 17
<212> TYPE: PRT
<213> ORGANISM: Artificial Sequence
<220> FEATURE:
<223> OTHER INFORMATION: Signal sequence of A. niger
      pectinemethylesterase PMeA ss

<400> SEQUENCE: 3

Met Val Lys Ser Ile Leu Ala Ser Val Phe Phe Ala Ala Thr Ala Leu
1               5                   10                  15

Ala

<210> SEQ ID NO 4
<211> LENGTH: 19
<212> TYPE: PRT
<213> ORGANISM: Artificial Sequence
<220> FEATURE:
<223> OTHER INFORMATION: Pro-sequence A.niger proline-specific
      endoprotease

<400> SEQUENCE: 4

Ala Arg Pro Arg Leu Val Pro Lys Pro Val Ser Arg Pro Ala Ser Ser
1               5                   10                  15

Lys Ser Ala

<210> SEQ ID NO 5
<211> LENGTH: 521
<212> TYPE: PRT
<213> ORGANISM: Artificial Sequence
<220> FEATURE:
```

<223> OTHER INFORMATION: Proline-specific endoprotease from Aspergillus niger comprising a PMeA signal sequence from A. niger

<400> SEQUENCE: 5

```
Met Val Lys Ser Ile Leu Ala Ser Val Phe Phe Ala Ala Thr Ala Leu
1               5                   10                  15

Ala Ala Arg Pro Arg Leu Val Pro Lys Pro Val Ser Arg Pro Ala Ser
            20                  25                  30

Ser Lys Ser Ala Ala Thr Thr Gly Glu Ala Tyr Phe Glu Gln Leu Leu
        35                  40                  45

Asp His His Asn Pro Glu Lys Gly Thr Phe Ser Gln Arg Tyr Trp Trp
    50                  55                  60

Ser Thr Glu Tyr Trp Gly Gly Pro Gly Ser Pro Val Val Leu Phe Thr
65                  70                  75                  80

Pro Gly Glu Val Ser Ala Asp Gly Tyr Glu Gly Tyr Leu Thr Asn Glu
                85                  90                  95

Thr Leu Thr Gly Val Tyr Ala Gln Glu Ile Gln Gly Ala Val Ile Leu
            100                 105                 110

Ile Glu His Arg Tyr Trp Gly Asp Ser Ser Pro Tyr Glu Val Leu Asn
        115                 120                 125

Ala Glu Thr Leu Gln Tyr Leu Thr Leu Asp Gln Ala Ile Leu Asp Met
    130                 135                 140

Thr Tyr Phe Ala Glu Thr Val Lys Leu Gln Phe Asp Asn Ser Thr Arg
145                 150                 155                 160

Ser Asn Ala Gln Asn Ala Pro Trp Val Met Val Gly Gly Ser Tyr Ser
                165                 170                 175

Gly Ala Leu Thr Ala Trp Thr Glu Ser Val Ala Pro Gly Thr Phe Trp
            180                 185                 190

Ala Tyr His Ala Thr Ser Ala Pro Val Glu Ala Ile Tyr Asp Tyr Trp
        195                 200                 205

Gln Tyr Phe Tyr Pro Ile Gln Gln Gly Met Ala Gln Asn Cys Ser Lys
    210                 215                 220

Asp Val Ser Leu Val Ala Glu Tyr Val Asp Lys Ile Gly Lys Asn Gly
225                 230                 235                 240

Thr Ala Lys Glu Gln Gln Ala Leu Lys Glu Leu Phe Gly Leu Gly Ala
                245                 250                 255

Val Glu His Phe Asp Asp Phe Ala Ala Val Leu Pro Asn Gly Pro Tyr
            260                 265                 270

Leu Trp Gln Asp Asn Asp Phe Ala Thr Gly Tyr Ser Ser Phe Phe Gln
        275                 280                 285

Phe Cys Asp Ala Val Glu Gly Val Glu Ala Gly Ala Ala Val Thr Pro
    290                 295                 300

Gly Pro Glu Gly Val Gly Leu Glu Lys Ala Leu Ala Asn Tyr Ala Asn
305                 310                 315                 320

Trp Phe Asn Ser Thr Ile Leu Pro Asp Tyr Cys Ala Ser Tyr Gly Tyr
                325                 330                 335

Trp Thr Asp Glu Trp Ser Val Ala Cys Phe Asp Ser Tyr Asn Ala Ser
            340                 345                 350

Ser Pro Ile Tyr Thr Asp Thr Val Gly Asn Ala Val Asp Arg Gln
        355                 360                 365

Trp Glu Trp Phe Leu Cys Asn Glu Pro Phe Phe Tyr Trp Gln Asp Gly
    370                 375                 380

Ala Pro Glu Gly Thr Ser Thr Ile Val Pro Arg Leu Val Ser Ala Ser
385                 390                 395                 400
```

Tyr Trp Gln Arg Gln Cys Pro Leu Tyr Phe Pro Glu Thr Asn Gly Tyr
            405                 410                 415

Thr Tyr Gly Ser Ala Lys Gly Lys Asn Ala Ala Thr Val Asn Ser Trp
        420                 425                 430

Thr Gly Gly Trp Asp Met Thr Arg Asn Thr Thr Arg Leu Ile Trp Thr
            435                 440                 445

Asn Gly Gln Tyr Asp Pro Trp Arg Asp Ser Gly Val Ser Ser Thr Phe
        450                 455                 460

Arg Pro Gly Gly Pro Leu Ala Ser Thr Ala Asn Glu Pro Val Gln Ile
465                 470                 475                 480

Ile Pro Gly Gly Phe His Cys Ser Asp Leu Tyr Met Ala Asp Tyr Tyr
                485                 490                 495

Ala Asn Glu Gly Val Lys Lys Val Val Asp Asn Glu Val Lys Gln Ile
            500                 505                 510

Lys Glu Trp Val Glu Glu Tyr Tyr Ala
            515                 520

<210> SEQ ID NO 6
<211> LENGTH: 1566
<212> TYPE: DNA
<213> ORGANISM: Artificial Sequence
<220> FEATURE:
<223> OTHER INFORMATION: Proline-specific endoprotease from Aspergillus
      niger comprising a PMeA signal sequence from A. niger

<400> SEQUENCE: 6

```
atggtcaagt ccatcctggc ctccgtcttc ttcgctgcca ctgctcttgc tgcaaggcct      60
cgtctcgttc ccaagcccgt ttctcgtccc gccagctcca agtccgctgc tactactggt     120
gaggcctact tgaacagct gttggaccac acaaccctg agaagggtac tttctcgcaa       180
agatactggt ggagcaccga gtactggggt ggtcccggat cccccgttgt cctgttcact     240
cccggtgagg tcagcgctga tggctacgag ggttatctga ccaacgagac tctcaccggt     300
gtctacgccc aggagattca gggtgctgtc atcctgatcg aacaccgata ctggggtgac     360 tcgtctcct acgaggtgct gaacgccgag actctccagt acttgaccct cgaccaggct     420
atccttgata tgacctactt cgccgaaacc gtcaagctcc agtttgacaa ctccacccgc     480
tccaacgctc agaacgctcc ttgggttatg gtcggcggca gctacagcgg tgctctgact     540
gcttggaccg agtccgttgc tcccggcacc ttctgggctt accacgccac ctctgctcct     600
gttgaggcca tctacgacta ctggcaatac ttctacccca ttcagcaggg tatggctcag     660
aactgctcca agatgtctc tcttgtagca gaatacgtcg acaagatcgg caagaacggc     720
actgccaagg agcaacaggc tctgaaggag cttttcggcc taggagcagt ggagcacttc     780
gacgacttcg ccgctgttct gcccaacggt ccttacctct ggcaagacaa cgactttgcc     840
accggttact cttctttctt ccagttctgt gatgccgtcg agggtgtcga ggctggtgct     900
gccgtcaccc ccgtcctga aggtgttggt ctggaaaagg cccttgctaa ctacgcgaac     960
tggttcaact ctaccatcct ccccgattac tgcgccagct acggctactg gactgacgag    1020
tggtccgtcg cctgcttcga ctcctacaac gcctcctctc ctatatacac cgacaccagc    1080
gttggtaacg ccgtcgaccg tcagtgggag tggttcctct gcaatgagcc cttcttttac    1140
tggcaggacg tgcccccga gggtacttca acgatagtac ccgcttagt gtccgcctcc    1200 tactggcagc gtcaatgtcc gttgtacttc cccgagacta acggttacac ctacggctcc    1260
gccaagggaa agaacgccgc caccgtcaac agctggaccg gtggctggga catgacccgt    1320
```

```
aacaccaccc gtctgatctg gacgaacggc caatacgacc cctggcgtga ctccggtgtc    1380
tcttccacct tccgccccgg tggtccctc gcttcgaccg ccaacgagcc cgtccagata     1440 ataccggtg gtttccattg ctccgacctc tacatggcag actactacgc caacgagggc     1500
gtcaagaagg ttgtcgacaa cgaagtcaaa caaatcaagg agtgggttga ggaatactac    1560
gcgtaa                                                               1566
```

PROLINE SPECIFIC ENDOPROTEASE

CROSS-REFERENCE TO RELATED APPLICATIONS

This application is a National Stage entry of International Application No. PCT/EP2015/061026, filed May 19, 2015, which claims priority to European Patent Application No. 14168866.3, filed May 19, 2014.

The present invention relates to a polypeptide having proline-specific endoprotease activity, a composition comprising the polypeptide, a nucleic acid encoding a proline-specific endoprotease, an expression vector comprising the nucleic acid encoding a proline-specific endoprotease, a recombinant host cell, a method for preparing proline-specific endoprotease and a process for preparing a food or feed product wherein the proline-specific endoprotease is used.

BACKGROUND

Proline-specific endoproteases are enzymes that hydrolyse a protein or peptide at a position where there is a proline in the protein or peptide.

A proline-specific endoprotease may for instance be derived from *Aspergillus niger* or *Penicillium chrysogenum*, such as disclosed in WO2002/046381 and WO2009/144269 respectively.

Other proline-specific endoproteases are known from WO2012/174127. WO2012/174127 discloses proline-specific protease from *Botryotinia, fuckeliana, Aspergillus clavatus, Sclerotinia sclerotiotum, Mycosphaerelly graminicola, Neuropspora crasse, Talaromyces stipitatus* and *Gibberella zeae*.

Proline-specific endoprotease can be used in several applications, for instance in the degradation of gluten (see for instance WO2005/027953 or WO2003/068170). Gluten is the insoluble protein fraction of cereals like wheat, rye, oat and barley. Gluten is a complex mixture of glutenin- and prolamine molecules which are thought to cause toxic effects, for instance in patients suffering from celiac disease. Celiac Sprue or celiac disease is considered to be an autoimmune disease. Patients suffering from Celiac Sprue need to follow a strict gluten-free diet, which is very difficult to follow because gluten is so widely used. The use or proline-specific endoprotease as a medicament or dietary supplement may alleviate the need for a strict gluten free diet (WO2003/068170).

Proline-specific endoproteases are also used for reducing haze in beer, wherein the proline-specific protease may be added during several stages of a beer production process for instance as disclosed in WO 2002/046381, or WO2007101888A2.

The aim of the present invention is an alternative proline-specific endoprotease with improved characteristics.

SUMMARY

In one aspect the present invention relates an isolated polypeptide having proline-specific endoprotease activity selected from the group consisting of i. a polypeptide comprising a mature polypeptide sequence of SEQ ID NO: 2;
ii. a polypeptide that has least 70%, 75%, 80%, 85%, 86%, 87%, 88%, 89%, 90%, 91%, 92%, 93%, 94%, 95%, 96%, 97%, 98% or 99% identity to a mature polypeptide sequence of SEQ ID NO: 2;
iii. a polypeptide encoded by a nucleic acid that hybridizes under medium stringency, preferably under high stringency conditions to the complementary strand of a mature polypeptide coding sequence of SEQ ID NO:1;
iv. a polypeptide encoded by a nucleic acid that has at least 70%, 75%, 80%, 85%, 90%, 91%, 92%, 93%, 94%, 95%, 96%, 97%, 98%, 99% or 100% identity to a mature polypeptide coding sequence of SEQ ID NO: 1;

In another aspect the present invention relates to a composition comprising a polypeptide as disclosed herein.

In one aspect the present invention relates to a nucleic acid that has at least 70%, 75%, 80%, 85%, 90%, 91%, 92%, 93%, 94%, 95%, 96%, 97%, 98%, 99% or 100% identity to a mature polypeptide coding sequence of SEQ ID NO: 1.

The present invention also relates to an expression vector comprising a polynucleotide encoding a polypeptide according to the present invention.

In another aspect the present invention relates to a host cell comprising a polynucleotide sequence, or an expression vector as disclosed herein.

In yet another aspect the present invention relates to a method for the preparation of a polypeptide, comprising cultivating a host cell as disclosed herein under conditions that allow expression of the polypeptide, and preparing the polypeptide.

In another aspect the present invention relates to a process for the preparation of a food or feed product comprising incubating an intermediate form of the food or feed product with a polypeptide as disclosed herein, and preparing the food product.

The present invention also relates to a food or feed product obtainable by a process as disclosed herein.

DEFINITIONS

The term "baked products" is herein defined as any product prepared from a dough or a batter. The product may have a soft or a crisp character and may be of a white, light or dark type. Baked products include, but are not limited to, bread such as for instance white, whole-meal or rye bread, French baguette-type bread, laminated dough products such as (Danish) pastry, croissants or puff pastry, pita bread, tortillas, tacos, cakes, pancakes, biscuits, cookies, doughnuts, bagels, pie crusts, muffins, steamed bread, and crisp bread. Types of baked products, methods to characterize and to produce them are known to those skilled in the art see for example "Baking Science and Technology", by E. J. Pyler, L. A. Gorton, 2008, (2 volumes) Sosland Publishing Company, Kansas, USA, or "Baked Products: Science, Technology and Practice" by S. P. Cauvain, L. S. Young, 2006, Blackwell Publishing Ltd, Oxford, UK.

The term "complementary strand" can be used interchangeably with the term "complement". The complement of a nucleic acid strand can be the complement of a coding strand or the complement of a non-coding strand. When referring to double-stranded nucleic acids, the complement of a nucleic acid encoding a polypeptide refers to the complementary strand of the strand encoding the amino acid sequence or to any nucleic acid molecule containing the same.

The term "control sequence" can be used interchangeably with the term "expression-regulating nucleic acid sequence". The term as used herein refers to nucleic acid sequences necessary for and/or affecting the expression of an operably linked coding sequence in a particular host organism or in vitro. When two nucleic acid sequences are operably linked, they usually will be in the same orientation and also in the same reading frame. They usually will be essentially contiguous, although this may not be required. The expression-regulating nucleic acid sequences, such as inter alia appropriate transcription initiation, termination, promoter, leader, signal peptide, propeptide, prepropeptide, or enhancer sequences; Shine-Dalgarno sequence, repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either endogenous or heterologous to a host cell. Each control sequence may be native or foreign to the nucleic acid sequence encoding the polypeptide. When desired, the control sequence may be provided with linkers for the purpose of introducing specific restriction sites facilitating ligation of the control sequences with the coding region of the nucleic acid sequence encoding a polypeptide. Control sequences may be optimized to their specific purpose.

A "dairy product" refers to any kind of milk-based product intended to be used as food, feed or beverage, including but not limited to cheese, milk, skimmed milk, acidified milk, butter milk, condensed milk, spreads, margarines, yoghurt, ice cream, milk powder, butter, EMC (Enzyme Modified Cheese), dulce de leche, coffee whitener; coffee creamer, cream, ghee, dairy analogue, etcetera. Cheese may be any kind of cheese, e.g. fresh cheese, hard cheese, curd cheese, cream cheese, white mould cheese, blue mould cheese and process cheese. Examples of fresh cheese are Ricotta, Cream cheese, Neufchatel or Cottage cheese. Examples of hard cheese are Chester, Danbo, Manchego, Saint Paulin, Cheddar, Monterey, Colby, Edam, Gouda, Muenster, Swiss type, Gruyere, Emmenthaler, Parmigiano Reggiano, Grana Padano, Parmesan, Pecorino, Provolone, and Romano. Examples of curd cheese such as Feta cheese, Quotija cheese, pasta filata cheese such as Mozzarella, and Queso fresco cheese. Examples of cream cheese are Philadelphia cheese. Examples of white mould cheese are Brie and Camembert cheese. Examples of blue mould cheese are Gorgonzola and Danish blue cheese.

As used herein, the term "endogenous" refers to a nucleic acid or amino acid sequence naturally occurring in a host.

Endopeptidases, endoproteinases or endoproteases are enzymes that able to break peptide bonds of nonterminal amino acids (i.e. within the protein), in contrast to exopeptidases, which break peptide bonds either from the amino or the carboxyl terminus. Endopeptidases do not tend to break down peptides into monomers, but result in relatively large peptide fragments. The specific generation of relatively large fragments is highly preferred in many food and feed related applications. A particular case of endopeptidase is the oligopeptidase, whose substrates are oligopeptides instead of proteins.

The term "expression" includes any step involved in the production of the polypeptide including, but not limited to, transcription, post transcriptional modification, translation, post-translational modification, and secretion.

An expression vector comprises a polynucleotide coding for a polypeptide, operably linked to the appropriate control sequences (such as a promoter, and transcriptional and translational stop signals) for expression and/or translation in vitro, or in the host cell of the polynucleotide.

The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e. a vector, which exists as an extra-chromosomal entity, the replication of which is independent of chromosomal replication, e.g., a plasmid, an extra-chromosomal element, a mini-chromosome, or an artificial chromosome. Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. The vector system may be a single vector or plasmid or two or more vectors or plasmids, which together contain the total DNA to be introduced into the genome of the host cell, or a transposon.

A host cell as defined herein is an organism suitable for genetic manipulation and one which may be cultured at cell densities useful for industrial production of a target product, such as a polypeptide according to the present invention. A host cell may be a host cell found in nature or a host cell derived from a parent host cell after genetic manipulation or classical mutagenesis. Advantageously, a host cell is a recombinant host cell.

A host cell may be a prokaryotic, archaebacterial or eukaryotic host cell. A prokaryotic host cell may be, but is not limited to, a bacterial host cell. An eukaryotic host cell may be, but is not limited to, a yeast, a fungus, an amoeba, an algae, a plant, an animal, or an insect host cell.

The term "heterologous" as used herein refers to nucleic acid or amino acid sequences not naturally occurring in a host cell. In other words, the nucleic acid or amino acid sequence is not identical to that naturally found in the host cell.

The term "hybridization" means the pairing of substantially complementary strands of oligomeric compounds, such as nucleic acid compounds.

Hybridization may be performed under low, medium or high stringency conditions. Low stringency hybridization conditions comprise hybridizing in 6× sodium chloride/sodium citrate (SSC) at about 45° C., followed by two washes in 0.2×SSC, 0.1% SDS at least at 50° C. (the temperature of the washes can be increased to 55° C. for low stringency conditions). Medium stringency hybridization conditions comprise hybridizing in 6×SSC at about 45° C., followed by one or more washes in 0.2×SSC, 0.1% SDS at 60° C., and high stringency hybridization conditions comprise hybridizing in 6×SSC at about 45° C., followed by one or more washes in 0.2×SSC, 0.1% SDS at 65° C.

A nucleic acid or polynucleotide sequence is defined herein as a nucleotide polymer comprising at least 5 nucleotide or nucleic acid units. A nucleotide or nucleic acid refers to RNA and DNA. The terms "nucleic acid" and "polynucleotide sequence" are used interchangeably herein.

A "peptide" refers to a short chain of amino acid residues linked by a peptide (amide) bonds. The shortest peptide, a dipeptide, consists of 2 amino acids joined by single peptide bond.

The term "polypeptide" refers to a molecule comprising amino acid residues linked by peptide bonds and containing more than five amino acid residues. The term "protein" as used herein is synonymous with the term "polypeptide" and may also refer to two or more polypeptides. Thus, the terms "protein" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity in the presence of a specific substrate under certain conditions may be referred to as enzymes. It will be understood that, as a result of the degeneracy of the genetic code, a multitude of nucleotide sequences encoding a given polypeptide may be produced.

An "isolated nucleic acid fragment" is a nucleic acid fragment that is not naturally occurring as a fragment and would not be found in the natural state.

The term "isolated polypeptide" as used herein means a polypeptide that is removed from at least one component, e.g. other polypeptide material, with which it is naturally associated. The isolated polypeptide may be free of any other impurities. The isolated polypeptide may be at least 50% pure, e.g., at least 60% pure, at least 70% pure, at least 75% pure, at least 80% pure, at least 85% pure, at least 80% pure, at least 90% pure, or at least 95% pure, 96%, 97%, 98%, 99%, 99.5%, 99.9% as determined by SDS-PAGE or any other analytical method suitable for this purpose and known to the person skilled in the art. An isolated polypeptide may be produced by a recombinant host cell.

A "mature polypeptide" is defined herein as a polypeptide in its final form and is obtained after translation of a mRNA into polypeptide and post-translational modifications of said polypeptide. Post-translational modifications include N-terminal processing, C-terminal truncation, glycosylation, phosphorylation and removal of leader sequences such as signal peptides, propeptides and/or prepropeptides by cleavage.

A "mature polypeptide coding sequence" means a polynucleotide that encodes a mature polypeptide.

The term "nucleic acid construct" is herein referred to as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

A "proline-specific endoprotease" is a protease that hydrolyses a protein or peptide at a position where the protein or peptide contains a proline-residue. A proline-specific endoprotease may have proline-specific endopotease and/or proline-specific oligopeptidase activity (EC3.4.21.26). A proline-specific endoprotease is preferably an enzyme that hydrolyses a peptide bond at the carboxy-terminal end of proline residues, resulting in a peptide and/or polypeptide fragment with a C-terminal proline.

The term "promoter" is defined herein as a DNA sequence that binds RNA polymerase and directs the polymerase to the correct downstream transcriptional start site of a nucleic acid sequence to initiate transcription.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, underexpressed or not expressed at all. The term "recombinant" is synonymous with "genetically modified" and "transgenic".

Sequence identity. Sequence identity, or sequence homology are used interchangeable herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region.

The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at http://www.ncbi.nlm.nih.gov/.

The term "substantially pure" with regard to polypeptides refers to a polypeptide preparation which contains at the most 50% by weight of other polypeptide material. The polypeptides disclosed herein are preferably in a substantially pure form. In particular, it is preferred that the polypeptides disclosed herein are in "essentially pure form", i.e. that the polypeptide preparation is essentially free of other polypeptide material. Optionally, the polypeptide may also be essentially free of non-polypeptide material such as nucleic acids, lipids, media components, and the like. Herein, the term "substantially pure polypeptide" is synonymous with the terms "isolated polypeptide" and "polypeptide in isolated form". The term "substantially pure" with regard to polynucleotide refers to a polynucleotide preparation which contains at the most 50% by weight of other polynucleotide material. The polynucleotides disclosed herein are preferably in a substantially pure form. In particular, it is preferred that the polynucleotide disclosed herein are in "essentially pure form", i.e. that the polynucleotide preparation is essentially free of other polynucleotide material. Optionally, the polynucleotide may also be essentially free of non-polynucleotide material such as polypeptides, lipids, media components, and the like. Herein, the term "substantially pure polynucleotide" is synonymous with the terms "isolated polynucleotide" and "polynucleotide in isolated form".

A "synthetic molecule", such as a synthetic nucleic acid or a synthetic polypeptide is produced by in vitro chemical or enzymatic synthesis. It includes, but is not limited to, variant nucleic acids made with optimal codon usage for host organisms of choice.

A synthetic nucleic acid may be optimized for codon use, preferably according to the methods described in WO2006/077258 and/or WO2008000632, which are herein incorporated by reference. WO2008/000632 addresses codon-pair optimization. Codon-pair optimization is a method wherein the nucleotide sequences encoding a polypeptide that have been modified with respect to their codon-usage, in particular the codon-pairs that are used, are optimized to obtain improved expression of the nucleotide sequence encoding the polypeptide and/or improved production of the encoded polypeptide. Codon pairs are defined as a set of two subsequent triplets (codons) in a coding sequence. Those skilled in the art will know that the codon usage needs to be adapted depending on the host species, possibly resulting in variants with significant homology deviation from SEQ ID NO: 1, but still encoding the polypeptide according to the invention.

As used herein, the terms "variant", "derivative", "mutant" or "homologue" can be used interchangeably. They can refer to either polypeptides or nucleic acids. Variants include substitutions, insertions, deletions, truncations, transversions, and/or inversions, at one or more locations relative to a reference sequence. Variants can be made for example by site-saturation mutagenesis, scanning mutagenesis, insertional mutagenesis, random mutagenesis, site-directed mutagenesis, and directed-evolution, as well as various other recombination approaches known to a skilled person in the art. Variant genes of nucleic acids may be synthesized artificially by known techniques in the art.

DETAILED DESCRIPTION

In one aspect the present invention relates to a polypeptide having proline-specific endoprotease activity, selected from the group consisting of
i. a polypeptide comprising a mature polypeptide sequence of SEQ ID NO: 2;
ii. a polypeptide that has least 70%, 75%, 80%, 85%, 86%, 87%, 88%, 89%, 90%, 91%, 92%, 93%, 94%, 95%, 96%, 97%, 98% or 99% identity to a mature polypeptide sequence of SEQ ID NO: 2;
iii. a polypeptide encoded by a nucleic acid that hybridizes under medium stringency, preferably under high stringency conditions to the complementary strand of a mature polypeptide coding sequence of SEQ ID NO:1;
iv. a polypeptide encoded by a nucleic acid that has at least 70%, 75%, 80%, 85%, 90%, 91%, 92%, 93%, 94%, 95%, 96%, 97%, 98%, 99% or 100% identity to a mature polypeptide coding sequence of SEQ ID NO: 1;

In one embodiment the present invention relates to a polypeptide that is an isolated, substantially pure, pure, recombinant, synthetic or variant polypeptide of the polypeptide as disclosed herein.

In another aspect the present invention relates an isolated polypeptide having proline-specific endoprotease activity comprising the amino acid sequence of SEQ ID NO: 2. A proline-specific endoprotease as disclosed herein may be derived from *Rasamsonia emersonii*. The wording "derived" or "derivable" from with respect to the origin of a polypeptide as disclosed herein, means that when carrying out a BLAST search with a polypeptide according to the present invention, the polypeptide according to the present invention may be derivable from a natural source, such as a microbial cell, of which an endogenous polypeptide shows the highest percentage homology or identity with the polypeptide as disclosed herein.

Advantageously, a polypeptide having prolinespecific endoprotease provided by the present invention is relatively thermostable. Surprisingly, a polypeptide according to the present invention was found to be more thermostable than a proline-specific endoprotease from *Aspergillus niger*. We found that a polypeptide according to the present disclosure had at least 50%, or at least 55%, or at least 60% residual activity after the polypeptide had been kept at a temperature of at least 70° C. for 15 min, such as at 70° C. for 15 min, or 71° C. for 15 min, wherein the activity is measured with Acetyl AlaAlaPro-para-nitroalinine (Ac-AAP-pNA) as a substrate. Accordingly, a proline-specific endoprotease as disclosed herein can be readily used in food applications, where there is a desire by the food industry to apply the enzyme at higher temperatures, for instance during mashing in a process for the preparation of beer.

Preferably, a polypeptide provided by the invention may be a polypeptide that has least 70%, 75%, 80%, 85%, 86%, 87%, 88%, 89%, 90%, 91%, 92%, 93%, 94%, 95%, 96%, 97%, 98% or 99% identity to the mature polypeptide sequence of SEQ ID NO: 2. A polypeptide according to SEQ ID NO: 2 comprises a pre-pro-sequence. Upon secretion of the polypeptide through a host cell's membrane, the pre-pro-sequence, such as amino acids 1 to 35, 1 to 36, 1 to 37, 1 to 38, 1 to 39, 1 to 40, 1 to 41, 1 to 42, 1 to 43, 1 to 44, 1 to 45, 1 to 46, 1 to 47, 1 to 48, 1 to 49, 1 to 50, or 1 to 51 of SEQ ID NO: 2 are removed. The mature polypeptide sequence having proline-specific endoprotease activity of SEQ ID NO:2 may comprise amino acids 35, 36, 37, 38, 39, 40, 41, 42, 43, 44, 45, 46, 47, 48, 49, 50 or 51 to amino acid 512, 513, 514, 515, 516, 517, 518, 519, 520 or 526 of SEQ ID NO:2, wherein the amino acid methionine at position 1 in SEQ ID NO: 2 is counted as number 1. The mature polypeptide sequence of SEQ ID NO: 2 may comprise or contain amino acids 36 to 526 of SEQ ID NO: 2, wherein the amino acid methionine at position 1 in SEQ ID NO: 2 is counted as number 1.

A polypeptide according to the present invention may be encoded by any suitable polynucleotide sequence. Typically a polynucleotide sequence is codon optimized, or a codon pair optimized sequence for expression of a polypeptide as disclosed herein in a particular host cell.

A polypeptide as disclosed herein may be encoded by a polynucleotide that hybridizes under medium stringency, preferably under high stringency conditions to the complementary strand of the mature polypeptide coding sequence of SEQ ID NO:1. SEQ ID NO: 1 is a codon optimized polynucleotide sequence for expression of a polypeptide as disclosed herein in an *Aspergillus niger* host cell.

A polypeptide as disclosed herein may also be encoded by a nucleic acid that has at least 70%, 75%, 80%, 85%, 90%, 91%, 92%, 93%, 94%, 95%, 96%, 97%, 98%, 99% or 100% identity to a mature polypeptide coding sequence of SEQ ID NO: 1.

A polypeptide having proline-specific endoprotease activity as disclosed herein may also be a variant of a mature polypeptide of SEQ ID NO: 2, comprising a substitution, deletion and/or insertion at one or more positions of the mature polypeptide SEQ ID NO: 2. A variant of the mature polypeptide of SEQ ID NO:2 may be an amino acid sequence that differs in 1, 2, 3, 4, 5, 6, 7, 8, 9, 10, 11 or 12 amino acids from the amino acids of of the mature polypeptide of SEQ ID NO:2.

In one embodiment the present invention features a biologically active fragment of a polypeptide as disclosed herein.

Biologically active fragments of a polypeptide of the invention include polypeptides comprising amino acid sequences sufficiently identical to or derived from the amino acid sequence of the proline-specific endoprotease protein (e.g., the mature amino acid sequence of SEQ ID NO:2), which include fewer amino acids than the full length protein but which exhibits at least one biological activity of the corresponding full-length protein. Typically, biologically active fragments comprise a domain or motif with at least one activity of the proline-specific endoprotease protein. A biologically active fragment may for instance comprise a catalytic domain. A biologically active fragment of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

The invention also features nucleic acid fragments which encode the above biologically active fragments of the proline-specific endoprotease protein.

A polypeptide according to the present invention may be a fusion protein. Techniques for producing fusion polypeptides are known in the art, and include ligating the coding sequences encoding the polypeptides so that they are in frame. Expression of the fused polypeptide is under control of the same promoter (s) and terminator. The hybrid polypeptides may comprise a combination of partial or complete polypeptide sequences obtained from at least two different polypeptides wherein one or more may be heterologous to a host cell. Such fusion polypeptides from at least two different polypeptides may comprise a binding domain from one polypeptide, operably linked to a catalytic domain from a second polypeptide. Examples of fusion polypeptides and signal sequence fusions are for example as described in WO2010/121933, WO2013/007820 and WO2013/007821.

A polypeptide according to the present invention may be derived from any suitable eukaryotic. A eukaryotic cell may be a mammalian, insect, plant, fungal, or algal cell.

A polypeptide according to the present invention may also be derived from a filamentous fungal cell or thermophilic filamentous fungal cell. Preferred filamentous fungal cells belong to a species of an *Acremonium, Aspergillus, Chrysosporium, Myceliophthora, Penicillium, Talaromyces, Rasamsonia, Thielavia, Fusarium* or *Trichoderma, Amorphotheca, Pseudocercosporella, Trametes, Rhizomucor, Calcarisporiella, Thermomyces, Thermoascus, Cornyascus, Myricoccum, Scytalidium, Chaetomium, Paecilomyces, Corynascus, Malbranchea, Stilbella, Thermomyces, Dactylomyces, Humicola, Chaetomium, Melanocarpus, Rhizomucor, Lentinula, Anaeromyces* genus, and most preferably belong to a species of *Aspergillus niger, Acremonium alabamense, Aspergillus awamori, Aspergillus foetidus, Aspergillus sojae, Aspergillus fumigatus, Talaromyces emersonii, Rasamsonia emersonii, Aspergillus oryzae, Chrysosporium lucknowense, Fusarium oxysporum, Myceliophthora thermophila, Trichoderma reesei, Thielavia terrestris, Penicillium chrysogenum, Amorphotheca resinae, Aureobasidium pullulans, Pseudocercosporella herpotrichoides, Trametes versicolor* 52J, *Rhizomucor pusillus, Calcarisporiella thermophila, Talaromyces thermophilus, Thermomyces lanuginosus, Thermoascus auratiacus, Cornyascus thermophilus, Myricoccum thermophilum, Scytalidium thermophilum, Myceliophthora hinnulea, Chaetomium thermophilum, Paecilomyces byssochlamydoides, Corynascus sepedonium, Malbranchea cinnamonmea, Thielavia australiensis, Stilbella thermophila, Thermomyces stellatus, Talaromyces emersonii, Dactylomyces thermophilus, Humicola hyalothermophilia, Acremonium thermophilum, Chaetomium olivicolor, Melanocarpus albomyces, Rhizomucor miehei, Lentinula edodes* or *Anaeromyces mucronatus*. A polypeptide preferably is derivable from *Rasamsonia emersonii*.

A polypeptide according to the present invention may be a naturally occurring polypeptide or a genetically modified or recombinant polypeptide.

A polypeptide as disclosed herein may be purified. Purification of a protein is known to a skilled person in the art.

In one aspect the present invention relates to a composition comprising a polypeptide as disclosed herein.

A composition as disclosed herein, may comprise a carrier, an excipient, an auxiliary enzyme, or other compounds. Typically a composition, or a formulation, comprises a compound with which a proline-specific endoprotease may be formulated. An excipient as used herein is an inactive substance formulated alongside with a polypeptide as disclosed herein, for instance sucrose or lactose, glycerol, sorbitol or sodium chloride. A composition comprising a polypeptide as disclosed herein may be a liquid composition or a solid composition. A liquid composition usually comprises water. When formulated as a liquid composition, the composition usually comprises components that lower the water activity, such as glycerol, sorbitol or sodium chloride (NaCl). A solid composition comprising a polypeptide as disclosed herein may comprise a granulate comprising the enzyme or the composition comprises an encapsulated polypeptide in liquid matrices like liposomes or gels like alginate or carrageenans. There are many techniques known in the art to encapsulate or granulate a polypeptide or enzyme (see for instance G. M. H. Meesters, "Encapsulation of Enzymes and Peptides", Chapter 9, in N. J. Zuidam and V. A. Nedović (eds.) "Encapsulation Technologies for Active Food Ingredients and food processing" 2010).

A composition as disclosed herein may also comprise a carrier comprising a polypeptide as disclosed herein. A polypeptide as disclosed herein may be bound or immobilized to a carrier by known technologies in the art.

The present invention also relates to a process for preparing a composition comprising a polypeptide as disclosed herein, which may comprise spray drying a fermentation medium comprising the polypeptide, or granulating, or encapsulating a polypeptide as disclosed herein, and preparing the composition.

In another aspect the present invention relates to a polynucleotide sequence encoding a polypeptide as disclosed herein, which has at least 70%, 75%, 80%, 85%, 90%, 95%, 96%, 97%, 98%, or 99% sequence identity to SEQ ID NO: 1, or to the mature polypeptide coding sequence of SEQ ID NO:1. A polynucleotide sequence as disclosed herein may comprise SEQ ID NO: 1, or may comprise the mature polypeptide coding sequence of SEQ ID NO:1.

In one other embodiment of the present invention a nucleic acid is disclosed that is an isolated, substantially pure, pure, recombinant, synthetic or variant nucleic acid of the nucleic acid of SEQ ID NO: 1. A variant nucleic acid sequence may for instance have at least 70% sequence identity to SEQ ID NO:1.

In another aspect, the present invention relates to an expression vector comprising a polynucleotide as disclosed herein operably linked to one or more control sequence(s) that direct expression of the polypeptide in an expression host cell.

There are several ways of inserting a nucleic acid into a nucleic acid construct or an expression vector which are known to a skilled person in the art, see for instance Sambrook & Russell, *Molecular Cloning: A Laboratory Manual*, 3rd Ed., CSHL Press, Cold Spring Harbor, N.Y., 2001. It may be desirable to manipulate a nucleic acid encoding a polypeptide of the present invention with control sequences, such as promoter and terminator sequences.

A promoter may be any appropriate promoter sequence suitable for a eukaryotic or prokaryotic host cell, which shows transcriptional activity, including mutant, truncated, and hybrid promoters, and may be obtained from polynucleotides encoding extracellular or intracellular polypeptides either endogenous (native) or heterologous (foreign) to the cell. The promoter may be a constitutive or inducible promoter. Preferably, the promoter is an inducible promoter, for instance a starch inducible promoter. Promoters suitable in filamentous fungi are promoters which may be selected from the group, which includes but is not limited to promoters obtained from the polynucleotides encoding *A. oryzae* TAKA amylase, *Rhizomucor miehei* aspartic proteinase, *Aspergillus* gpdA promoter, *A. niger* neutral alpha-amylase, *A. niger* acid stable alpha-amylase, *A. niger* or *A. awamori* glucoamylase (glaA), *A. niger* or *A. awamori* endoxylanase (xlnA) or beta-xylosidase (xlnD), *T. reesei* cellobiohydrolase I (CBHI), *R. miehei* lipase, *A. oryzae* alkaline protease, *A. oryzae* triose phosphate isomerase, *A. nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the polynucleotides encoding *A. niger* neutral alpha-amylase and *A. oryzae* triose phosphate isomerase), and mutant, truncated, and hybrid promoters thereof.

Any terminator which is functional in a cell as disclosed herein may be used, which are known to a skilled person in the art. Examples of suitable terminator sequences in filamentous fungi include terminator sequences of a filamentous fungal gene, such as from *Aspergillus* genes, for instance from the gene *A. oryzae* TAKA amylase, the genes encoding *A. niger* glucoamylase (glaA), *A. nidulans* anthranilate synthase, *A. niger* alpha-glucosidase, trpC and/or *Fusarium oxysporum* trypsin-like protease.

In another aspect the present invention relates to a host cell comprising a nucleic acid construct or an expression vector as disclosed herein. A suitable host cell may be a mammalian, insect, plant, fungal, or algal cell, or a bacterial cell. A suitable host cell may be a fungal cell, for instance from the genus *Acremonium, Aspergillus, Chrysosporium, Fusarium, Myceliophthora, Penicillium, Rasamsonia, Talaromyces, Thielavia, Trichoderma, Saccaromyces, Kluyveromyces, Pichia*, for instance *Aspergillus niger, Aspergillus awamori, Aspergillus foetidus, A. oryzae, A. sojae, Talaromyces emersonii, Rasamsonia emersonii Chrysosporium lucknowense, Fusarium oxysporum, Myceliophthora thermophila, Thielavia terrestris* or *Trichoderma reesei* or, *Saccharomyces cerevisiae, Kluyveromyces lactis, Pichia pastoris*

A host cell may be a recombinant or transgenic host cell. The host cell may be genetically modified with a nucleic acid construct or expression vector as disclosed herein with standard techniques known in the art, such as electroporation, protoplast transformation or conjugation, for instance as disclosed in Sambrook & Russell, *Molecular Cloning: A Laboratory Manual*, 3rd Ed., CSHL Press, Cold Spring Harbor, N.Y., 2001.

In one aspect, the present invention relates to a process for the production of a polypeptide as disclosed herein comprising cultivating a host cell in a suitable fermentation medium under conditions conducive to the production of the polypeptide and producing the polypeptide. A skilled person in the art understands how to perform a process for the production of a polypeptide as disclosed herein depending on a host cell used, such as pH, temperature and composition of a fermentation medium. Host cells can be cultivated in shake flasks, or in fermenters having a volume of 0.5 or 1 liter or larger to 10 to 100 or more cubic meters. Cultivation may be performed aerobically or anaerobically depending on the requirements of a host cell.

Advantageously a polypeptide as disclosed herein is recovered or isolated from the fermentation medium.

A polypeptide having proline-specific endoprotease activity or a composition comprising a polypeptide as disclosed herein may be used in a large variety of applications, for instance in the production of a food or feed product, such as in the production of a protein hydrolysate. Several food proteins contain highly allergenic subfractions which may be even toxic to specific individuals, such as gluten that contains prolamines with proline-rich peptide sequences. These proteins can be subjected to the new enzyme to alleviate their antigenicity or toxicity.

A group of people to which gluten is toxic are individuals suffering from Celiac Sprue. Celiac Sprue, also known as celiac disease, is an autoimmune disease of the small intestine caused by the ingestion of gluten proteins from cereals, such as alpha-gliadin from wheat, hordein from barley, secalin from rye and avenin from oats.

Accordingly, a polypeptide having proline-specific endoprotease activity or a composition comprising a polypeptide as disclosed herein may be used in the preparation of a dietary supplement or as a medicament in the treatment of a patient suffering from Celiac Sprue and/or in the treatment of gluten intolerant people.

A polypeptide as disclosed herein may also be used as a processing aid to hydrolyse gluten in a food product.

Accordingly the present invention relates to a process for the preparation of a food or feed product comprising incubating an intermediate form of a food or feed product with a polypeptide or composition comprising the polypeptide as disclosed herein and preparing the food or feed product. A food product in a process as disclosed herein includes a beverage, such as beer, wine or fruit juice, or a baked product, or a dairy product, but is not limited thereto.

Incubating an intermediate form of a food or feed product with a polypeptide or composition comprising the polypeptide as disclosed herein may comprise adding the polypeptide or composition comprising the polypeptide to the intermediate form of the food or feed product.

A process for the preparation of a food product may be a process for the preparation of beer. Usually, a process for the preparation of beer comprises mashing of malt to obtain a mash and filtering the mash to obtain a wort, boiling the wort for instance with hop, and fermenting the wort by inoculating the wort with yeast. Following the fermentation, a process for the preparation of beer typically comprises a maturation and a stabilisation phase and usually also a filtration phase, depending on the type of beer that is produced.

An intermediate form of a food product may be any suitable form of a food product during the preparation of the food product. An intermediate form of beer may for instance be a mash, a wort, a fermentation broth, or a green beer. Green beer as used herein is a beer that results from a primary fermentation and typically may contain some unsettled yeast and undesirable flavour components. An intermediate form of bread may for instance be a dough or a batter. Advantageously, a polypeptide having proline-specific endoprotease activity or a composition comprising the polypeptide according to the present invention is incubated with a mash during mashing in a process for the preparation of beer. Surprisingly, a significant amount of haze-active proteins was reduced by a polypeptide according to the present invention during mashing. Consequently, the formation of haze in the final beer can be prevented. It is advantageous that a polypeptide having proline-specific endoprotease activity according to the present invention is active during mashing, since after mashing the separated wort is boiled and the enzyme is inactivated. This is advantageous since it is undesirable that enzymes are active in a final food product, such a beer.

Mashing is a process during which starch is broken down into sugars by natural enzymes present in the grain, known to a skilled person in the art. Typically, mashing comprises bringing a malt, i.e. a mixture of a milled grain such a malted barley and water, step-wise to a temperature of about 45-52° C. to a temperature of 71 to 76 during a certain length of time, which is known to a skilled person in the art. Usually, mashing comprises bringing the malt to a temperature of 45-52° C., then to a temperature of 60 to 65° C., then a temperature of about 71 to 76° C., and optionally to a final temperature of 76 to 79° C.

After the mashing, the liquid fraction also called the "wort" is separated from the solid fraction. Subsequently, the wort is typically boiled with further ingredients such as hop. During boiling of wort enzymes present in the wort are inactivated.

In one embodiment, a process for the preparation of a beer comprises incubating a mash with a polypeptide or a composition comprising a polypeptide as disclosed herein, and preparing the beer.

Haze-active proteins are proline-rich proteins which may interact with polyphenols to form protein-polyphenol aggregates. These protein-polyphenol aggregates cause the formation of haze, also called "chill haze" in beer. Accordingly, in one aspect the present invention relates to the use of a polypeptide as disclosed herein, or a composition as disclosed in the reduction of haze in a beverage. A beverage as used herein may be a beer.

A food product and/or an intermediate form of a food product may comprise gluten.

It was found that a polypeptide having proline-specific endoprotease activity as disclosed herein was capable of hydrolysing the toxic epitopes in gluten into non-toxic fragments. Accordingly, in one aspect the present invention relates to the use of a polypeptide or a composition comprising the polypeptide as disclosed herein in the reduction of gluten in a food product.

A process for the preparation of a food product according to the present disclosure may comprise a step of pasteurizing the food product. Pasteurization usually comprises heating a food product, or an intermediate form of a food product, for instance by bringing the food product or intermediate form of a food product to a temperature of between 60 to 68° C. between 10 to 20 min, or between 12 and 18 min, or to a temperature of between 70-74° C., such as about 72° C. for at least 5, 10 or 15 seconds.

A food product in a process as disclosed herein may also be a protein hydrolysate. Accordingly, the present disclosure relates to a process for the preparation of a protein hydrolysate, comprising contacting a protein substrate with a polypeptide or a composition as disclosed herein, and producing the protein hydrolysate. A protein hydrolysate may be prepared from any suitable a protein substrate, for instance a protein substrate that is rich in proline residues, such as gluten in cereals or caseins in bovine milk.

In one aspect the present invention relates to a food product obtainable by a process for the preparation of a food product as disclosed herein.

The following examples illustrate the invention.

EXAMPLES

Materials and Methods

Example 1. Cloning, Expression and Recovery Proline-Specific Endoprotease (PEP) BC2G079

Example 1.1. Cloning and Expression

The protein sequence of the proline-specific endoprotease (PEP) *Rasamsonia emersonii* is shown in SEQ ID NO: 2 and called PEP BC2G079.

A codon-adapted DNA sequence for expression of this protein in *Aspergillus niger* was designed containing additional restriction sites for subcloning in an *Aspergillus* expression vector. Codon adaptation was performed as described in WO 2008/000632. The codon optimized DNA sequence for *A. niger* of the gene encoding the PEP protein of SEQ ID: NO: 2 is shown in SEQ ID NO: 1.

Figure 1:
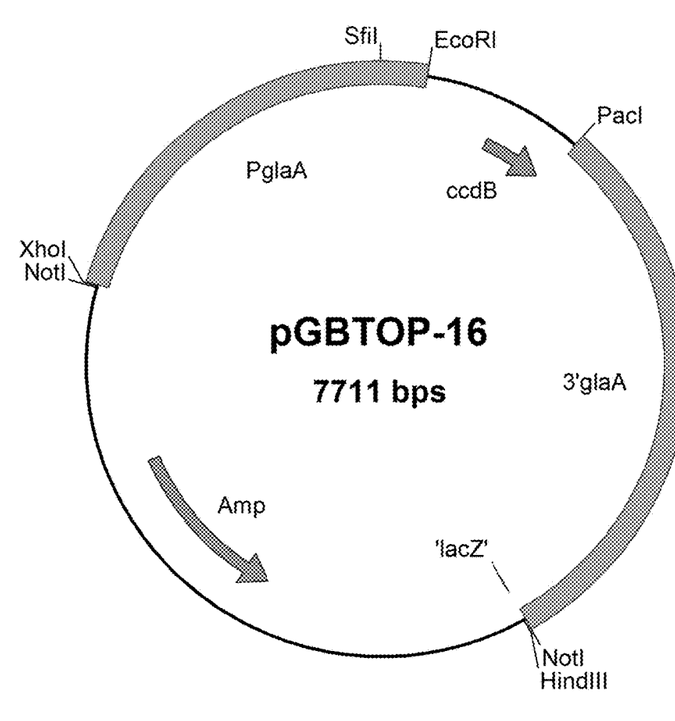
FIG. 1: pGBTOP-16 vector used for cloning of the GLA gene. The pGBTOP-16 vector is derived from the pGBTOP-12 vector described in WO 2011/009700. In addition to pGBTOP-12, it contains the ccdB gene from *E. coli* for positive selection for presence of an insert between the EcoRI and PacI cloning sites. The PacI restriction site replaces the SnaBI restriction site present in pGBTOP-12. This vector is linearized by NotI digestion prior to transformation.

The translational initiation sequence of the glucoamylase glaA promoter was modified into 5'-CACCGTCAAA ATG-3' and an optimal translational termination sequence 5'-TAAA-3' was used in the generation of the expression construct (as also detailed in WO2006/077258). A DNA fragment containing a.o. part of the glucoamylase promoter and the PEP encoding gene was synthesized completely, purified and digested with EcoRI and PacI. The pGBTOP-16 vector (FIG. 1) was linearized by EcoRI/PacI digestion and the linearized vector fragment was subsequently purified by gel-extraction. The DNA fragment containing the PEP coding region was cloned into the pGBTOP-16 vector resulting in pGBTOP-PEP. Subsequently, *A. niger* GBA 306 (ΔglaA, ΔpepA, ΔhdfA, adapted BamHI amplicon, ΔamyBII, ΔamyBI, ΔamyA alpha-amylase and glucoamylase negative strain) was transformed with linearized pGBTOP-PEP vector by NotI-digestion, in a co-transformation protocol with linearized pGBAAS-4, with strain and methods as described in WO 2011/009700 and references therein, and selected on acetamide containing media and colony purified according to standard procedures. Transformation and selection was performed as described in WO 98/46772 and WO 99/32617. Strains containing the PEP gene encoding PEP BC2G079 were selected via PCR with primers specific for the PEP gene to verify presence of the pGBTOP-PEP expression cassette. A single transformant was selected, named PEP1, and further replica-plated to obtain a single strain inoculum.

Example 1.2. Production of PEP BC2G079 in *A. niger* PEP1 Strain

Fresh *A. niger* PEP-1 spores were prepared. 4 shake flasks with 100 ml fermentation medium 1 (10% w/v Corn Steep Solids, 1% w/v glucose.$H_2O$, 0.1% w/v $NaH_2PO_4.H_2O$, 0.05% w/v $MgSO_4.7H_2O$, 0.025% w/v Basildon, pH 5.8) in 500 ml shake flasks with baffle were inoculated with $10^7$ spores. These pre-cultures were incubated at 34° C. and 170 rpm for 16-24 hours. From the pre-cultures, 50 ml was used for inoculation of 1 shake flasks with 1 liter Fermentation medium 2 (15% w/v maltose, 6% w/v bacto-soytone, 1.5% w/v $(NH_4)_2SO_4$, 0.1% w/v $NaH_2PO_4.H_2O$, 0.1% w/v $MgSO_4.7H_2O$, 0.1 w/v L-arginine, 8% w/v Tween-80, 2% w/v Basildon, 2% w/v MES pH 5.1) in a 5 liter shake flask size and shaken at 34° C. and 170 rpm. After 3, 4, 5, and 6 days incubation the pH of the culture was lowered to pH 5.0 using 2 N HCl and samples from each of these time points were analysed for PEP activity. 50 mL samples were taken and the supernatant was separated from the biomass by centrifugation and subsequent filtering. The sample with the highest activity was used to characterize the PEP produced.

Example 1.3. Production of the Reference Proline-Specific Endoprotease from *A. niger*

The proline-specific endoprotease from *A. niger* is known from WO2002/046381. The protein sequence of proline-specific endoprotease (PEP) from *A. niger* is shown in SEQ ID NO: 5, wherein the first 17 amino acids are a signal sequence of pectinemethylesterase of *A. niger* (PMeA ss; SEQ ID NO: 3) and the following part comprises 19 amino acids of the prosequence of *A. niger* proline specific endoprotease (SEQ ID NO: 4).

Expression and production of PEP from *A. niger* was performed in the same way as described under example 1.1. and 1.2. The *A. niger* PEP is used as the reference enzyme in Example 2.

Example 2. Proline-Specific Endoprotease (PEP) Activity Measurements

100 μL of culture supernatant as produced in Example 1, diluted in 0.1 M sodium acetate buffer at pH4.5 with 50 mM NaCl, was incubated with 100 μL 6 mM Ac-AAP-pNA (acetyl-AlaAlaPro-paranitroaniline from Selleckchem or CPC Scientific; purity >95.0% based on HPLC analysis) in 0.1 M NaAc buffer at pH4.5 with 50 mM NaCl, in a Nunc 96 well flat bottom MTP (micro-titer plate). After 60 minutes at 20° C. the reaction was stopped by adding 40 μL of 1 M HCl. The pNA which had been liberated by PEP was measured in a Tecan MTP spectrophotometer at 405 nm (A405) (www.tecan.com). The blank was prepared by mixing the diluted culture supernatant with the substrate solution which had been mixed with the HCl solution beforehand. The activity is expressed in pNASU's. 1 pNASU is the amount of enzyme which liberates from Ac-AAP-pNA in 1 hour the amount of pNA that corresponds to an increase in absorption at 405 nm of 1 OD, using the conditions as described above. The A405 should not be below the blank value at the start of the reaction, or above 2.5 at the end of the reaction, nor may the A405 exceed the linear range of the spectrophotometer that is used.

TABLE 1

Relative activity of PEP BC2G079, as compared to the PEP reference.

| Description | Activity (pNASU/ml) | Specific Activity (pNASU/mg) |
|---|---|---|
| PEP reference | 100% | 100% |
| PEP BC2G079 | 171% | 150% |

In order to compare the specific activity of PEP BC2G079 to the reference PEP the protein concentrations of respectively the PEP BC2G079 and the reference PEP were determined by measuring the absorbance at 280 nm after gel filtration over a PD10 column to remove low molecular weight compounds which might interfere with the 280 nm measurement. Quantitative SDS-PAGE carried out as described in WO2013160316 showed that more than 80% of the protein present is the PEP of interest. The extinction coefficient was calculated using the Prot Param tool as can be accessed through the website http://web.expasy.org/protparam/. The mature sequence of SEQ ID NO 2 (amino acids 36-526) was used for the calculating the extinction coefficient for PEP BC2G079 ($A280^{1cm,1mg/ml}$=2.81). The mature sequence of SEQ ID NO 5 (amino acids 37-521) was used for the reference PEP ($A280^{1cm,1mg/ml}$=3.05).

Example 3. Thermal Stability Proline-Specific Endoprotease (PEP) BC2G079

To assess the thermal stability of PEP BC2G079 the activity assay was preceded by an incubation of 100 μL aliquots of a tenfold dilution of the culture supernatant produced in Example 1 in buffer (0.1 M NaAc pH 4.5, with 50 mM NaCl) at 55° C. and 65° C. for 15 min in a PCR plate in a PCR machine. After the 15 min incubation the samples were rapidly cooled to 25° C. in the PCR machine. The pNASU/mL of every sample was measured. The initial activity measured before incubation at elevated temperature (0 minutes) is used as reference (100%) to determine the residual activity.

TABLE 2

Proline-specific endoprotease activity of PEP BC2G079 after 15 minutes incubation at 55° C. and 65° C.

| Description | Residual activity after 15' at 55° C. (pNASU) | Residual activity at after 15' at 65° C. (pNASU) |
|---|---|---|
| PEP BC2G079 | 105% | 84% |

The results in Table 1 show that PEP BCG079 derived from *Rasamsonia emersonii* is relatively stable at a temperature of 65 degrees Celsius.

Example 5. Thermal Stability Profile PEP BC2G079 Compared to Reference PEP from *A. niger*

To assess the thermal stability profile of PEP BC2G079 under more extreme conditions the activity assay was preceded by heating step. 100 μL aliquots of a culture supernatant as produced in Example 1 were diluted tenfold in buffer (0.1 M NaAc pH 4.5, with 50 mM NaCl) and heated over a range of temperatures in a PCR plate in a PCR machine. After the 15 min incubation period the samples were rapidly cooled to 25° C. in the PCR machine. The pNASU/mL of every sample was measured. The initial activity measured before incubation at elevated temperature (0 minutes) was used as reference (100%) to determine the residual activity. The results in table 3 show that a proline-specific endoprotease (BCG079) from *Rasamsonia emersonii* is substantially more thermostable compared to the reference proline-specific endoprotease from *A. niger*.

TABLE 3

Proline-specific endoprotease residual activity of PEP BC2G079 and reference PEP from *A. niger* after 15 minutes incubation at various temperatures.

| Incubation temperature (° C.) | PEP reference Residual Activity (pNASU/ml) | BC2G079 Residual Activity (pNASU/ml) |
|---|---|---|
| 51.4 | 100% | |
| 54.4 | 97% | |
| 59.0 | 93% | |
| 63.5 | | 100% |
| 64.5 | 76% | |
| 66.6 | | 91% |
| 69.3 | 24% | |
| 71.2 | | 65% |
| 72.4 | 1% | |
| 74.0 | 0% | |
| 76.7 | | 11% |
| 81.4 | | 0% |

Example 6. pH Activity Profile of PEP BC2G079

To assess the operational pH range of PEP BC2G079, the culture supernatant and the Ac-AAP-pNA substrate were both diluted in buffers ranging from pH 3.5 to pH 7 (0.1 M citric acid/$Na_2HPO_4$, with 50 mM NaCl). Subsequently, 100 μL of the diluted supernatant was mixed with 100 μL of the 6 mM Ac-AAP-pNA substrate solution in a 96 wells flat bottom MTP. The reaction was stopped after 60 min at 20° C. with addition of 40 μL 1 M NaOH. The activity of the PEP was measured by the increase in absorbance at 405 nm. The results in Table 4 show that the highest activity for BC2G079 was observed at pH=5.0, which was set at 100% while the reference PEP from *A. niger* shows highest activity (100%) at pH=5.5. Overall the pH-activity profile of BC2G079 has shifted 0.5 pH unit towards more acidic pH operating conditions. As a consequence below pH 5.5 PEP BC2G079 exhibits higher relative activity compared to the PEP reference.

TABLE 4 pH activity profile of PEP BC2G079

| pH | PEP BC2G079 (pNASU/ml) | Reference PEP (pNASU/ml) |
|---|---|---|
| 3.5 | 59% | 54% |
| 4.0 | 81% | 68% |
| 4.5 | 97% | 78% |
| 5.0 | 100% | 97% |
| 5.5 | 86% | 100% |
| 6.0 | 63% | 92% |
| 6.5 | 41% | 60% |
| 7.0 | 24% | 34% |

Example 7. Mashing Trial 7.1. Methods

To determine the PNACU's an aliquot of 100 μL is mixed in a Nunc 96 flat bottom MTP with 100 μL 6 mM Ac-AAP-pNA in 0.1 M NaAc buffer, pH4.5, containing 50 mM NaCl. The increase in OD at 405 nm is recorded as function of time in a Tecan MTP spectrophotometer. PNACU's should be calculated from the linear part of the curve, preferably the initial slope. The assay is performed at 20° C. In order to measure the increase in OD over a sufficiently long time span while staying within the linear range of the detector the enzyme sample is diluted accordingly with 0.1 M NaAc buffer, pH 4.5, with 50 mM NaCl. One PNACU is the amount of enzyme which liberates in one hour from Ac-AAP-pNA the amount of pNA that corresponds to an increase of the absorption at 405 nm of one OD unit.

Haze active proteins were measured with a Tannometer using the Pfeuffer operating instructions for this method. Tannic acid was added to the samples and the haze measured under 90 degree scatter angle expressed in EBC units and reported for the addition of 2.5, 5 and 10 mg/l tannic acid.

Gliadin in the wort was determined with a competitive Elisa (RIDASCREEN® Gliadin competitive (R-Biopharm) as a measure for the gluten content.

7.2. Degradation of Haze-Active Proteins and Gluten During Mashing

The degradation of haze-active proteins and gluten by a thermostable PEP BC2G079 enzyme in a mashing process was determined and compared to the performance of the less thermostable PEP reference enzyme from *A. niger*. In one mashing experiment 5 mL of thermostable PEP BC2G079 containing 460 PNACU/ml was added to 200 mL of mash. In another mashing experiment 5 mL of the reference PEP containing 460 PNACU/ml was added. The enzymes were added at the start of the mashing process A third mash was performed, wherein the same volume of tap water was added instead of enzyme solution, to serve as a blank comparison.

Lab scale mashing trials were performed in a mashing bath (Lochner Labor technik, Germany). 80 gram of milled standard EBC malt was used in 200 ml of water. The mash was step-wise heated as shown in Table 5. The mashes were stirred continuously at 100 rpm during the mashing process. At the end of the mashing the mash was filtered over a filter paper (Macherey-Nagel, MN614 ¼, 320 mm diameter). The filtrate is called the wort. A sample was taken from the wort and analysed for the presence of haze sensitive proteins and gluten and determination of proline-specific endoprotease activity (pNASU).

TABLE 5

Mashing scheme

| time from start (min) | temperature (° C.) |
| --- | --- |
| 0 | 50 |
| 15 | 50 |
| 28 | 63 |
| 43 | 63 |
| 55 | 75 |
| 70 | 75 |
| 73 | 78 |
| 78 | 78 |

The results on degradation of haze sensitive proteins and gliadin are shown in Table 6 and Table 7.

TABLE 6

Amount of haze active proteins (measured in EBC units) in wort samples from mashes wherein no PEP was present and mashes that have been treated with a thermostable PEP BC2G079 and a reference PEP

| | EBC haze after addition of tannic acid Wort samples | | |
| --- | --- | --- | --- |
| Tannic acid | No PEP | Reference PEP | Thermostable PEP |
| 2.5 mg/l | 1.2 | 0.7 | 0.3 |
| 5 mg/l | 4.0 | 2.7 | 0.8 |
| 10 mg/l | 9.3 | 6.2 | 1.5 |

TABLE 7

Gliadin content in wort from mashes wherein no PEP was present and mashes that have been treated with a thermostable PEP BC2G079 and a reference PEP

| Wort samples | Gliadin in ppm |
| --- | --- |
| No PEP | 362 |
| Reference PEP | 135 |
| Thermostable PEP | 82 |

The results in Table 6 and 7 show that a thermostable PEP like BC2G079 is much more efficient in degrading haze-active proteins and gliadin during the mashing process compared to the less thermostable reference PEP. The residual activity of PEP was also determined at the end of the mashing process described above (Table 8). Only the thermostable PEP BC2G079 is still active while the reference PEP is completely inactivated. The higher thermostability correlates with the degradation of haze sensitive protein and removal of gliadin. The mashing data show that a thermostable PEP is advantageous in the mashing as the thermostability significantly extends the time that the PEP is active in the mashing.

TABLE 8

Residual activity PEP at the end of the mashing

| | Residual Activity at the end of the mashing (pNASU/ml) |
| --- | --- |
| Reference PEP | 0% |
| Thermostable PEP | 41% |

Example 8. Determination of the Molecular Mass of the Mature PEP BC2G079 with LC-MS For LC-MS analysis of the mature BC2G079 PEP, 100 µl sample of the supernatant of a fermentation medium produced in Example 1.2. was mixed with 100 µl 20% TCA (Chem Lab NV, Belgium). This solution was put on ice for 1 hour. After precipitation of the proteins, the sample was centrifuged at 14000 rpm and 4° C., for 15 min. After centrifugation the supernatant was removed and the pellet was washed once with 500 µl acetone (−20° C., Sigma-Aldrich, Netherlands) and centrifuged at 14000 rpm and 4° C. for 10 min. The supernatant was removed and the pellet was dissolved in 50 µl 50 mM NaOH (Sigma-Aldrich, Netherlands) and then 350 µl 100 mM $NH_4HCO_3$ (Sigma-Aldrich, Netherlands) was added. Then 200 µl of the sample was reduced and alkylated. For reduction, 5 µl TCEP (Sigma-Aldrich, Netherlands) was added to the solution and incubated at room temperature in a thermomixer at 1000 rpm for 30 min. For the alkylation 5 µl of 550 mM IAA (Iodoacetamide, Sigma-Aldrich, Netherlands) was added and incubated in a thermomixer at 1000 rpm in the dark for 30 min. In order to deglycosylate the sample, 20 µl PNGase F (Promega, USA) was added. The sample was incubated in thermomixer at 1000 rpm at 37° C. overnight. The next day 1% Formic Acid (Merk, Germany) was added in order to dilute the sample to a concentration of 50 µg/ml. The protein concentration was measured on the Qubit quantitative protein assay (Life technologies). The sample was analyzed on the Acquity I-class—Synapt G2-S (Waters, UK), with the following parameters: column: Waters Acquity UPLC BEH300 C4 1.7 μm 300 Å pore size 2.1×50 mm; column temperature: 75° C.; injection volume: 1 μl; mobile phase A: Formic Acid 0.1% in Mili-Q (Biosolve, Netherlands); mobile phase B: Formic Acid 0.1% in Acetonitrile (Biosolve, Netherlands). A 15 minutes gradient was applied to the column by varying phase A and B (from 20 to 50% B). The MS detector settings were: acquisition mass range 500-3500 m/z, scan time 1 sec, positive ESI, TOF MS Resolution mode, with data correction using Leu-Enk (Sigma-Aldrich, Netherlands) as lock mass on the fly during the run. Data spectral deconvolution, charge state stripping, was performed with a Waters MassLynx MaxEnt1 software tool: output mass resolution=1 Da/channel; damage model: Gaussian (FWHH=0.750 Da; minim intensity ratios=33% left and right); iterate to converge.

After correction for alkylation and deglycosylation the mass spectra show a major species with a molecular mass corresponding to amino acids 36-526 of SEQ ID NO 2. In addition there is a minor species with a molecular mass corresponding to amino acids 41-526 of SEQ ID NO 2. As a consequence the N-terminus of the major species in the mature PEP BC2G079 sample corresponds to RDPLHGPT and the N-terminus of the minor species starts at GPTNAS. Both species show multiple peaks in the mass spectrum. Each peak shifted by 57 Da or a multitude of 57 Da indicating a difference in alkylation. A single alkylation adds 57 Da per cysteine. In the spectra the addition of 1, 3, 5 and 7 IAA's were observed in agreement with the presence of 7 cysteines in the amino acid sequence. Observed masses for the fully alkylated major and minor species are respectively 55218 Da and 54598 Da. As deglycosylation adds a further 1 Da per deglycosylated site the data suggest that 6-7 of the theoretical 8 glycosylation sites are actually glycosylated.

The invention claimed is:

1. A recombinant polypeptide selected from the group consisting of:
  i. a polypeptide that has between 85% and 99% sequence identity to the mature polypeptide sequence of SEQ ID NO:2; and
  ii. a polypeptide encoded by a nucleic acid that has between 85% and 99% sequence identity to the mature polypeptide coding sequence of SEQ ID NO: 1, wherein said polypeptide has between 85% and 99% sequence identity to the mature polypeptide sequence of SEQ ID NO:2; and
  wherein the polypeptide has proline-specific endoprotease activity.

2. The recombinant polypeptide according to claim 1, wherein the mature polypeptide sequence of SEQ ID NO:2 comprises amino acids 36 to 526 of SEQ ID NO:2, wherein methionine at position 1 in SEQ ID NO:2 is counted as 1.

3. The recombinant polypeptide according to claim 1 that has between 90% and 99% sequence identity to the mature polypeptide sequence of SEQ ID NO:2.

4. The recombinant polypeptide according to claim 1 that has between 95% and 99% sequence identity to the mature polypeptide sequence of SEQ ID NO:2.

5. A composition comprising a polypeptide selected from the group consisting of:
  i. a polypeptide that has 85% sequence identity to the mature polypeptide sequence of SEQ ID NO:2; and
  ii. a polypeptide encoded by a nucleic acid that has 85% sequence identity to the mature polypeptide coding sequence of SEQ ID NO: 1, wherein said polypeptide has 85% sequence identity to the mature polypeptide sequence of SEQ ID NO:2; and,
  wherein the polypeptide has proline-specific endoprotease activity, and
  wherein said composition is a liquid composition comprising glycerol or sorbitol, or is a solid granulated or encapsulated polypeptide.

6. The composition according to claim 5, further comprising a carrier, an excipient, or an auxiliary enzyme.

7. A nucleic acid encoding a proline-specific endoprotease, which has 85%, 90%, 95%, 96%, 97%, 98%, or 99% sequence identity to the mature polypeptide encoding sequence of SEQ ID NO:1.

8. An expression vector comprising the nucleic acid according to claim 7 operably linked to one or more control sequence(s) that direct expression of the polypeptide in a host cell.

9. A recombinant host cell comprising:
  a nucleic acid encoding a proline-specific endoprotease, which has between 85% and 99% sequence identity to the mature polypeptide encoding sequence of SEQ ID NO:1; or
  an expression vector thereof comprising said nucleic acid, operably linked to one or more control sequence(s) that direct expression of the polypeptide in a host cell;
  wherein the nucleic acid is heterologous to the host cell.

10. A method for preparation of the recombinant polypeptide according to claim 1, comprising cultivating a host cell comprising a nucleic acid that has between 85% and 99% sequence identity to the mature polypeptide coding sequence of SEQ ID NO:1 in a suitable fermentation medium, under conditions that allow expression of the polypeptide, and preparing the polypeptide.

11. The method according to claim 10, further comprising recovering the polypeptide.

12. A process for preparation of a food or feed product comprising bringing an intermediate form of a food or feed product into contact with:
  (a) a polypeptide having proline-specific endoprotease activity selected from the group consisting of:
    i. a polypeptide comprising the mature polypeptide sequence of SEQ ID NO:2;
    ii. a polypeptide that has least 85% identity to the mature polypeptide sequence of SEQ ID NO:2; and
    iii. a polypeptide encoded by a nucleic acid that has at least 85% identity to the mature polypeptide coding sequence of SEQ ID NO:1;
  (b) a composition comprising said polypeptide, or
  (c) a composition comprising said polypeptide, and a carrier or an excipient;
  and preparing the food or feed product.

13. The process according to claim 12, wherein the food product is a beverage.

14. The process according to claim 13, wherein the intermediate form of the food product is a mash.

15. The process according to claim 14, wherein the process further comprises incubating the polypeptide with the mash during mashing.

16. The process according to claim 12, wherein the food product comprises gluten.

17. The process according to claim 16, wherein the food product is a beer.

18. The process of claim 12, wherein:
  the mature polypeptide sequence of SEQ ID NO:2 comprises amino acids 36 to 526, amino acids 37 to 526, amino acids 39 to 526, amino acids 40 to 526, or amino acids 41 to 526 of SEQ ID NO:2, wherein methionine at position 1 of SEQ ID NO:2 is counted as 1; and
  the polypeptide has at least 50% residual activity on acetyl AlaAlaPro-para-nitroaniline (Ac-AAP-pNA) as a substrate after the polypeptide has been kept at a temperature of at least 70° C. for 15 minutes.

19. The process according to claim 12, wherein the beverage is a beer.

20. A food or feed product obtainable by the process according to claim 12.

21. A product comprising the polypeptide according to claim 1 or a composition thereof that can reduce haze in a beverage.

* * * * *